US007335668B2

(12) United States Patent
Ikeda et al.

(10) Patent No.: US 7,335,668 B2
(45) Date of Patent: Feb. 26, 2008

(54) PHARMACEUTICAL COMPOSITION FOR THERAPY OF INTERSTITIAL CYSTITIS

(75) Inventors: Ken Ikeda, Tsukuba (JP); Makoto Takeuchi, Tsukuba (JP)

(73) Assignee: Astellas Pharma Inc. (JP)

( * ) Notice: Subject to any disclaimer, the term of this patent is extended or adjusted under 35 U.S.C. 154(b) by 555 days.

(21) Appl. No.: 10/479,798

(22) PCT Filed: Jul. 8, 2002

(86) PCT No.: PCT/JP02/06904

§ 371 (c)(1),
(2), (4) Date: Dec. 5, 2003

(87) PCT Pub. No.: WO03/006019

PCT Pub. Date: Jan. 23, 2003

(65) Prior Publication Data

US 2004/0138252 A1    Jul. 15, 2004

(30) Foreign Application Priority Data

Jul. 10, 2001 (JP) ............................. 2001-209041

(51) Int. Cl.
A01N 43/90 (2006.01)
A61K 31/44 (2006.01)
C07D 453/02 (2006.01)
(52) U.S. Cl. ...................... 514/305; 546/137
(58) Field of Classification Search .............. 514/202, 514/305; 546/137
See application file for complete search history.

(56) References Cited

U.S. PATENT DOCUMENTS 6,017,927 A    1/2000  Takeuchi et al.

FOREIGN PATENT DOCUMENTS

WO    WO 96/20194    7/1996

OTHER PUBLICATIONS

Theoharides et al. Expert Opinion on Investigational Drugs (2001,10, 3, p. 521-546).*
Birder et al. (J of Urology, 168, 1989-1995, Nov. 1997).*
Cruz et al. (Int Urogynecol Pelvic Floor Dysfunct, 1998, 9, 4, 214-20).*
Mealy N., et al., *YM-905: Treatment of Urinary Incontinence Muscarinic $M_3$ Antagonist*, Drugs of the Future, 1999, pp. 6871-6874, vol. 24 No. 8.
Kobayashi. S, et al., *Effects of YM905, a Novel Muscarinic $M_3$-Antagonist, On Experimental Models of Bowel Dysfunction In Vivo*, Jpn. J. Pharmacol. 2001, pp. 281-288, vol. 86, No. 3.
Lazzeri M., et al., *Intravesical Resiniferatoxin for the Treatment of Hypersensitive Disorder: A Randomized Placebo Controlled Study*, J. Urology, Sep. 2000, pp. 676-679, vol. 164.
Hall C., et al., *Interstitial Cystitis: An Overview and Discussion of Treatment Options*, Prim. Care Update Ob/Gyns, 1995, pp. 181-187, vol. 2, No. 5.

* cited by examiner

Primary Examiner—Sreeni Padmanabhan
Assistant Examiner—Umamaheswari Ramachandran
(74) Attorney, Agent, or Firm—Finnegan, Henderson, Farabow, Garrett & Dunner, LLP

(57) ABSTRACT

A depressant of capsaicin-sensitive sensory nerve, containing quinuclidin-3'-yl 1-phenyl-1,2,3,4-tetrahydroisoquinoline-2-carboxylate or a salt thereof as an active ingredient, specifically a therapeutic drug of interstitial cystitis, hypersensitive disorder of the lower urinary tract, and/or abacterial prostatitis.

2 Claims, 1 Drawing Sheet

PHARMACEUTICAL COMPOSITION FOR THERAPY OF INTERSTITIAL CYSTITIS

Figure 1:
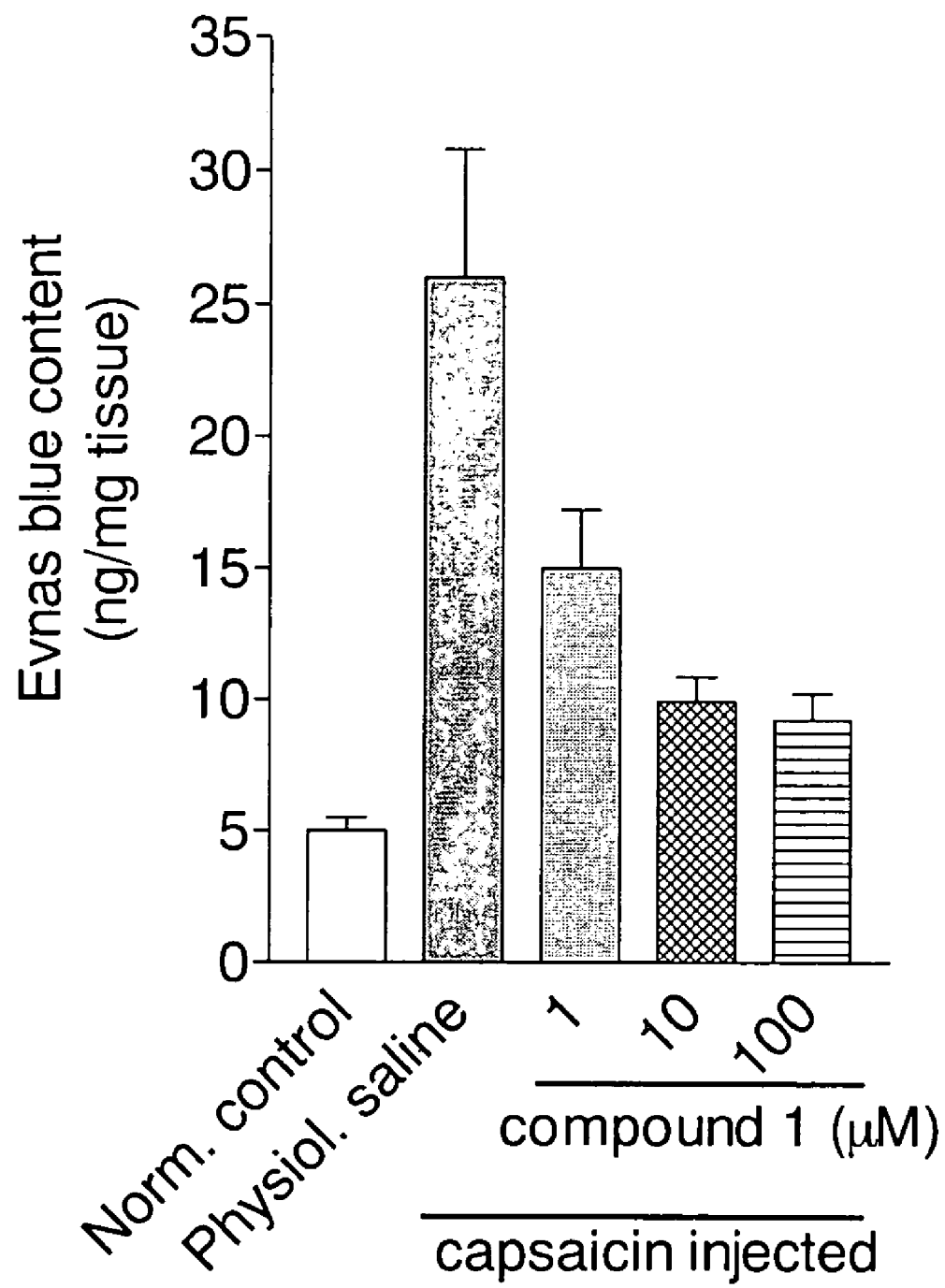

This application is the National Stage of International Application No. PCT/JP02/06904, filed Jul. 8, 2002.

TECHNICAL FIELD

The present invention relates to a depressant of capsaicin-sensitive sensory nerve, specifically a therapeutic drug of interstitial cystitis, hypersensitive disorder of the lower urinary tract, and/or abacterial prostatitis.

BACKGROUND ART

Interstitial cystitis is sterile cystitis that occurs primarily in women and is a disease exhibiting symptoms such as severe pain and urinary frequency, urinary urgency, nocturia, and a sense of suprapubic pressure or pain when the bladder is filled, which is alleviated after urination (*Expert Opinion on Invest Drug*, 10: p.521).

The abacterial prostatitis is sterile prostatitis that is diagnosed on the basis of white blood cell counts and quantitative determination of bacteria in urine specimens according to the disease classification of Drach, et al. (1978), and is thought as a variant of condition of interstitial cystitis (*Expert Opinion on Invest Drug*, 10: p.521).

Hypersensitive disorder of the lower urinary tract as referred to herein means the state of exhibiting a pain by hypersensitivity in any one of the bladder or urethra and occurs even in the absence of infectious diseases in the urinary tract or apparent pathological changes in the bladder wall and urethra. During the infusion period of cytometrogram, there is no increase in the intravesical pressure (lower than 15 cm $H_2O$); nonetheless, the physiological bladder volume is small, and these finding are characteristics for this disorder (*Diagnostic Criteria of the Hypersensitive Disorders by N J R George in Sensory Disorders of the Bladder and Urethra*, edited by N J R George and J A Gosling, Springer-Verlag, Berilin, 1986, pp.17-29).

With respect to drugs to treat interstitial cystitis, the intravesical administration of dimethyl sulfoxide (DMSO) is approved by Food and Drug Administration in the United States, and its mechanism of action is considered to be desensitization of capsaicin-sensitive sensory nerves (*Expert Opinion on Invest Drug*, 10: p.521 and *J. Urol.*, 158: pp.1989-1995). Also, it is reported that the intravesical instillation of capsaicin or resiniferatoxin, that is with the same pharmacological action, improves pain or other symptoms of interstitial cystitis in clinical testing (*J. Urol.*, 157, Suppl: p.254 (1997) and *J. Urol.*, 163, Suppl: p.60 (2000)).

In addition, it is suggested that resiniferatoxin is effective against symptoms, such as urinary urgency and bladder pain, due to hypersensitive disorder of the lower urinary tract that is not accompanied with interstitial cystitis nor the typical pathological change (*J. Urol.*, 164: pp.676-679 (2000)). Accordingly, it is considered that drugs having a depressant action on capsaicin-sensitive sensory nerves are effective for improving pain and symptoms in interstitial cystitis, hypersensitive disorder of the lower urinary tract, and/or abacterial prostatitis.

Thus, for the purpose of creating a novel therapeutic drug capable of improving pain and symptoms in interstitial cystitis, hypersensitive disorder of the lower urinary tract, and abacterial prostatitis, the present inventors made extensive and intensive investigations on a compound having a depressant action on capsaicin-sensitive sensory nerves.

DISCLOSURE OF THE INVENTION

As a result, the present invention has found that quinuclidin-3'-yl 1-phenyl-1,2,3,4-tetrahydroisoquinoline-2-carboxylate (hereinafter abbreviated as "Compound A") or a salt thereof has a depressant effect on capsaicin-sensitive sensory nerves and is useful for the therapy of interstitial cystitis, hypersensitive disorder of the lower urinary tract, and/or abacterial prostatitis, leading to accomplishment of the invention.

Compound A or a salt thereof is described in International Patent Publication No. 96/20194 and is disclosed to have binding action selective for muscarine $M_3$ receptors and inhibitory effects on rat rhythmic bladder contraction and indicated to be useful as a therapeutic drug for urogenital diseases such as urinary incontinence and pollakiuria/urinary frequency. However, the improvement of pain of urogenital diseases exhibiting painful symptoms is neither indicated nor disclosed, and the therapy of specific diseases such as interstitial cystitis, hypersensitive disorder of the lower urinary tract, and abacterial prostatitis is not disclosed at all.

Also, it has hitherto been considered that anticholinergic drugs (antimuscarinics) have only a minor role in the drug therapy of interstitial cystitis (*Primary Care Update Obstetrics & Gynecology*, 2: pp.181-187).

As shown in Test Example 1 described later, Compound A, when intravesically instilled, exhibited a depressant action on capsaicin-sensitive sensory nerve at urinary concentrations of 1 μM and more. On the other hand, from the results of Test Example 2, the concentration of urinary excreted Compound A is calculated to be about 1.9 μM when giving 10 mg per day orally and about 3.6 μM when giving 20 mg per day orally.

Accordingly, it is considered that Compound A or salts thereof have an inhibitory activity on capsaicin-sensitive sensory nerves within the bladder by oral administration and are effective for improving pain and symptoms such as urinary urgency in interstitial cystitis, hypersensitive disorder of the lower urinary tract, and/or abacterial prostatitis.

Specifically, the invention relates to a pharmaceutical composition for inhibition of capsaicin-sensitive sensory nerve, containing quinuclidin-3'-yl 1-phenyl-1,2,3,4-tetrahydroisoquinoline-2-carboxylate or a pharmaceutically acceptable salt thereof as an active ingredient, and specifically to a pharmaceutical composition for therapy of a urogenital disease selected from interstitial cystitis, hypersensitive disorder of the lower urinary tract, and abacterial prostatitis.

Also, the invention relates to use of quinuclidin-3'-yl 1-phenyl-1,2,3,4-tetrahydroisoquinoline-2-carboxylate or a pharmaceutically acceptable salt thereof for the production of a depressant of capsaicin-sensitive sensory nerve. The invention relates to use of quinuclidin-3'-yl 1-phenyl-1,2,3,4-tetrahydroisoquinoline-2-carboxylate or a pharmaceutically acceptable salt thereof for the production of a therapeutic drug of a urogenital disease selected from interstitial cystitis, hypersensitive disorder of the lower urinary tract, and abacterial prostatitis.

Also, the invention relates to a method of depressing capsaicin-sensitive sensory nerves, including administering a patient with a therapeutically effective amount of quinuclidin-3'-yl 1-phenyl-1,2,3,4-tetrahydroisoquinoline-2-carboxylate or a pharmaceutically acceptable salt thereof. The invention relates to a method of therapy of a urogenital disease selected from interstitial cystitis, hypersensitive disorder of the lower urinary tract, and abacterial prostatitis, including administering a patient with a therapeutically effective amount of quinuclidin-3'-yl 1-phenyl-1,2,3,4-tetrahydroisoquinoline-2-carboxylate or a pharmaceutically acceptable salt thereof.

The invention will be described below in more detail.

The active ingredient of the drug of the invention is quinuclidin-3'-yl 1-phenyl-1,2,3,4-tetrahydroisoquinoline-2-carboxylate (compound A) or a pharmaceutically acceptable salt thereof. As such salts, are enumerated the salts described in the foregoing International Patent Publication No. 96/20194. Specific examples acid addition salts of inorganic acid such as hydrochloric acid, hydrobromic acid, hydroiodic acid, sulfuric acid, nitric acid, and phosphoric acid, or organic acids such as formic acid, acetic acid, propionic acid, oxalic acid, malonic acid, succinic acid, fumaric acid, maleic acid, lactic acid, malic acid, tartaric acid, citric acid, methanesulfonic acid, ethanesulfonic acid, aspartic acid, and glutamic acid; and quaternary ammonium salts with halogen atom ions, triflates, tosylates, mesylates, etc. Above all, succinic acid salts are particularly preferable.

Also, since the active ingredient (Compound A) has asymmetric carbon atoms, an optically active substance is existed, and hence the active ingredient includes mixtures of diastereomers or enantiomers and isolated isomers thereof. Also, the active ingredient of the invention includes all of hydrates and solvates such as ethanol and crystal polymorphisms. In the invention, a succinic acid salt of (+)-(1S,3'R)-quinuclidin-3'-yl 1-phenyl-1,2,3,4-tetrahydroisoquinoline-2-carboxylate (solifenacin) is particularly preferable.

These compounds are readily available by the production process as described in the foregoing International Patent Publication No. 96/20194 or according to that production process.

The drug of the invention can be prepared as oral solid preparations, oral liquid preparations or injections using an organic or inorganic carrier, an excipient, and other additives suitable for oral or parenteral administration according to the customary manner. Since the active ingredient of the drug of the invention has excellent oral absorbing property, the drug of the invention is suitable for oral preparations. Oral solid preparations that patients can easily take themselves and are convenient in storage and conveyance are the most preferable.

Examples of oral solid preparations include tablets, powders, fine granules, granules, capsules, pills, and sustained release products. In such solid compositions, at least one active substance is mixed with at least one inert diluent such as lactose, mannitol, glucose, microcrystalline cellulose, starch, corn starch, polyvinylpyrrolidone, and magnesium metasilicate aluminate. The composition may contain additives other than inert diluents such as binders such as hydroxypropyl cellulose and hydroxypropylmethyl cellulose (HPMC); lubricants such as magnesium stearate, polyethylene glycol, starch, and talc; disintegrating agents such as cellulose calcium glycolate and carmellose calcium; stabilizers such as lactose; dissolution aids such as glutamic acid and aspartic acid; plasticizers such as polyethylene glycol; coloring agents such as titanium oxide, talc, and yellow iron oxide according to the customary manner. If desired, the tablets or pills may be coated with a sugar coating such as sugar, gelatin, agar, pectin, hydroxypropyl cellulose, and hydroxypropylmethyl cellulose phthalate, or a gastric-soluble or intestinal soluble film.

The oral liquid preparations include pharmaceutically acceptable emulsions, solutions, suspensions, syrups and elixirs and contain a generally employed inert diluent such as purified water and ethanol. This composition may contain an auxiliary agent such as wetting agents and suspending agents, a sweetener, a flavor, an aromatic, or an antiseptic, in addition to the inert diluent.

The injections such as intravenous injections, intramuscular injections, and subcutaneous injections include sterile aqueous or non-aqueous solutions, suspensions and emulsions. Examples of diluents for aqueous solutions or suspensions include distilled water and physiological saline. Examples of diluents for non-aqueous solutions or suspensions include propylene glycol, polyethylene glycol, vegetable oils such as olive oil, alcohols such as ethanol, and Polysolvate 80. Such a composition may further contain auxiliary agents such as an antiseptic, a wetting agent, an emulsifier, a dispersant, a stabilizer (such as lactose), and a dissolution aid (such as glutamic acid and aspartic acid). These compositions are sterilized by, for example, filtration through a bacteria-holding filter, compounding with an anti-bacterial agent, or irradiation. Further, these can be used by producing a sterile solid composition and dissolving it in sterile water or a sterile solvent for injection before use.

The dose of the active ingredient compound of the invention is properly determined depending on the individual case while taking into account the administration route, symptom of a patient, age of the subject to be administered, sex, etc. In the case of oral administration, the active ingredient can be usually administered in a dose of from about 1 to 100 mg/day, and preferably from 5 to 50 mg/day per adult once or dividedly twice.

Incidentally, the drug of the invention can be used in combination with other drugs that are used for therapy of urogenital diseases simultaneously or after elapsing for a while. Examples of drugs that can be used in combination with the drug of the invention include oral drugs such as pentosan sulfate, anti-inflammatory steroids, and antihistamines; and intravesical injections such as Bacillus Calmette-Guerin and doxorubicin.

BRIEF EXPLANATIONB OF THE DRAWING

FIG. 1 shows inhibitory effects of Compound 1 on capsaicin-induced extravasation of Evans blue in the mouse bladder.

BEST MODE FOR CARRYING OUT THE INVENTION

The invention will be hereunder described in detail with reference to the following Examples and Test Examples, but it should not be construed that the invention is limited to these Examples. Incidentally, Compound 1 as used in the following Examples and so on means a succinic acid salt of (+)-(1S,3'R)-quinuclidin-3'-yl 1-phenyl-1,2,3,4-tetrahydroisoquinoline-2-carboxylate (solifenacin).

EXAMPLE 1

Capsule Preparation

TABLE 1

|  | 1-mg Capsule | 10-mg Capsule | 100-mg Capsule |
| --- | --- | --- | --- |
| Compound 1 | 1.0 mg | 10.0 mg | 100.0 mg |
| Lactose | 199.0 mg | 190.0 mg | 100.0 mg |
| Total | 200.0 mg | 200.0 mg | 200.0 mg |

Components as shown in Table 1 were mixed and filled in a capsule to produce capsule preparations.

TEST EXAMPLE 1

Inhibitory Action of Compound 1 against Plasma Protein Extravasation Induced by Capsaicin in the Mouse Bladder (Method)

(1) Used Animal:

In the experiment, four or five female Balb/c mice (Japan SLC, Inc.) per group were used.

(2) Measurement of Plasma Protein Extravasation:

A catheter was inserted into the bladder of a mouse anesthetized with urethane (intraperitoneally administered with 0.15 ml of a 20% solution per mouse) via the urethra, and after emptying the bladder, a physiological saline or drug solution was injected. This catheter was prepared by blunting the tip of a 24-guage hypodermic needle and making a side hole at 2 mm from the newly prepared tip. About one hour after the instillation into the bladder, extravascular leakage of plasma proteins due to inflammatory reaction caused by stimulation of the capsaicin-sensitive sensory nerve according to the method of Maggi, et al. (Nauny-Schmiedeberg's *Arch. Pharmacol.*, 336: pp.546-555(1987)). That is Evans blue (30 mg/kg) a dye bound by plasma proteins and capsaicin (300 μg/kg) were administered to the mouse from the tail vein, and precisely five minutes after the administration, the mouse was killed by cervical dislocation, then the bladder was removed. After removing urine and blood remaining in the tissue, the dye in the organs was quantitatively determined. Evans blue dye was extracted from the bladder by placing the tissue in 150 μL of formamide overnight, and was quantitatively determined by measuring light absorbance at a wavelength of 620 nm of 100 μL supernatant in a 96-well microplate. In addition, the content of Evans blue dye in one milligram of wet tissue was calculated. Moreover, the mouse intravesically instilled with physiological saline and intravenously administered with a capsaicin-free Evans blue solution served as a normal control.

(3) Test Drug and Other Reagents:

Compound 1 was dissolved and diluted in physiological saline, and then administered into the bladder at a volume of 100 μL per mouse. Capsaicin and formamide were purchased from Wako Pure Chemical Industries, Ltd., and Evans blue was purchased from Aldrich. As the vehicle for capsaicin and Evans blue, physiological saline containing 0.1% dimethyl sulfoxide and 0.1% Tween 80 was used in a volume of 10 mL/kg.

(4) Statistic Processing:

Results were shown as [(mean values)±(standard errors of the mean)]. The Student's t-test was used to determine the significance of difference between the group of mice receiving intravesicla saline and stimulated with capsaicin e and the group of normal control mice. With respect to inhibitory effects of Compound 1 in the mice administered with capsaicin, a significance was determined using the Dunnett's t-test by comparison with the group intravesically injected with physiological salloeing the one-way analysis of variance. In these tests, the statistical significance was judged in the case where the p value was less than 5%.

(Results)

The experimental results are shown in FIG. 1. (The p value by comparison between the normal control group and the physiological saline group according to the Student t-test was 0.0027; the p value of the analysis of variance in the capsaicin-treated groups was 0.0033; and the p value, as determined by the Dunnett's t-test when comparing with the physiological saline group, for 1, 10 and 100 μM groups of Compound 1 when was 0.043, 0.0053 and 0.0023, respectively.) Capsaicin increased the Evans blue dye content in the mouse bladder by about 5 times as compared with the normal control group. Compound 1 injected intravesically at concentrations of 1, 10 and 100 μM reduced capsaicin-induced increases in the dye content by 52%, 76% and 80%, respectively. These changes brought about a statistically significant difference. Therefore, Compound 1 as infused intravesically at concentrations of 1 μM or more inhibited the extravascular leakage of plasma proteins in the bladder due to the inflammatory reaction induced by stimulation of the capsaicin-sensitive sensory nerve.

TEST EXAMPLE 2

Amount (of Compound 1) Excreted to Urine After Oral Administration to Humans (Method)

For the purpose of evaluating orally administered Compound 1 for the pharmacokinetics, tolerability and safety of, healthy subjects were repeatedlyadministered with Compound 1 at a dose of 10 mg or 20 mg per day for 15 days. To determine the amount compound 1 excreted into urine as the non-metabolized substance, their urine was collected for 24 hours after the final administration. To the urine sample were added a sodium bicarbonate solution and an internal standard substance, then, the mixture was extracted with tert-butyl methyl ether, and the organic layer was evaporated. The residue was dissolved in a mixed solution of acetic acid and methanol, and Compound 1 was separated by high-performance liquid chromatography. Detection of Compound 1 was carried out by mass spectrometry.

(Results)

The results are shown in Table 2.

TABLE 2

| Dose of Compound 1 | Sex | Excretion amount in urine (mg/day) |
| --- | --- | --- |
| 10 mg/day | Male | 0.911 |
|  | Female | 0.907 |
| 20 mg/day | Male | 1.844 |
|  | Female | 1.690 |

Assuming that the daily urine volume is about one liter (*Review of Medical Physiology*, 13$^{th}$ Edition, p.643), the mean concentration in urine of Compound 1 (molecular weight: 480) was calculated to be about 1.9 μM for oral administration of 10 mg per day and about 3.6 μM for oral administration of 20 mg per day.

From the results of Test Example 1 and Test Example 2, it is considered that, since Compound 1 can inhibit the inflammation in the bladder induced by stimulation of the capsaicin-sensitive sensory nerve when orally given to an adult at doses from 10 to 20 mg per day, Compound 1 is useful for the therapy of a urogenital disease selected from interstitial cystitis, hypersensitive disorder of the lower urinary tract, and abacterial prostatitis.

Also, the effect of the invention can also be confirmed by clinical tests to a patient with interstitial cystitis, hypersensitive disorder of the lower urinary tract or abacterial prostatitis and animal tests reflecting the pathology of such a disease.

INDUSTRIAL APPLICABILITY

According to the invention, it is possible to provide an oral therapeutic drug of interstitial cystitis, hypersensitive disorder of the lower urinary tract, and/or abacterial prostatitis.

The invention claimed is:

1. A method of depressing capsaicin-sensitive sensory nerves, comprising administering to a patient a therapeutically effective amount of quinuclidin-3'-yl 1-phenyl-1,2,3,4-tetrahydroisoquinoline-2-carboxylate or a pharmaceutically acceptable salt thereof.

2. The method according to claim 1, in which an oral preparation is administered.

* * * * *